United States Patent [19]
Branch et al.

[11] Patent Number: 5,154,947
[45] Date of Patent: Oct. 13, 1992

[54] METHOD FOR APPLYING BIOCIDAL CLOTHES DRYER ADDITIVE TO LAUNDERED FABRICS

[75] Inventors: Charles E. Branch, Norwalk; Thomas E. Robitaille, Portland, both of Conn.

[73] Assignee: Olin Corporation, Cheshire, Conn.

[21] Appl. No.: 679,467

[22] Filed: Apr. 2, 1991

[51] Int. Cl.$^5$ ............................................... B05D 3/12
[52] U.S. Cl. ........................................ 427/242; 34/9; 424/404
[58] Field of Search ............... 427/242; 424/404; 252/8.6; 34/9

[56] References Cited

U.S. PATENT DOCUMENTS

| | | | |
|---|---|---|---|
| 2,809,971 | 10/1957 | Bernstein et al. | 546/6 |
| 3,159,640 | 12/1964 | McClure et al. | 260/294.8 |
| 4,073,996 | 2/1978 | Bedenk et al. | 428/274 |
| 4,443,222 | 4/1984 | Morris et al. | 8/189 |
| 4,818,436 | 4/1989 | French et al. | 252/400.23 |
| 4,935,061 | 6/1990 | French et al. | 106/170 |
| 4,957,908 | 9/1990 | Nelson | 514/55 |

*Primary Examiner*—Evan Lawrence
*Attorney, Agent, or Firm*—Dale L. Carlson

[57] ABSTRACT

The present invention relates to a method for imparting biocidal protection to clothing or other fabrics which comprises contacting the clothing or other fabrics with a biocidally effective amount of pyrithione acid, or salt(s) thereof, or combinations thereof, in an automatic laundry dryer. Also disclosed is a transfer substrate containing a biocide consisting essentially of pyrithione acid, or salt(s) thereof, or combinations thereof, said biocide being present in or on said transfer substrate in an amount sufficient to impart antimicrobial activity to clothing or other fabric in an automatic clothes dryer.

2 Claims, No Drawings

METHOD FOR APPLYING BIOCIDAL CLOTHES DRYER ADDITIVE TO LAUNDERED FABRICS

FIELD OF THE INVENTION

This invention relates generally to a process for imparting biocidal properties to textiles and fabric, and, more specifically, to a process employing pyrithione salts in treating clothes and other fabrics during the dryer cycle in order to impart biocidal activity thereto.

BACKGROUND OF THE INVENTION

Pyrithione acid (1-hydroxy-2-pyridinethione) and various salts thereof are well-known biocides exhibiting broad spectrum anti-bacterial and anti-fungal activity. Illustrative applications are disclosed, for example, in U.S. Pat. No. 4,818,436 which discloses the use of pyrithiones in metal working fluids, and U.S. Pat. No. 4,935,061 which discloses their use in paints. Zinc pyrithione is widely used in hair care products such as shampoos.

The use of fabric treating articles and processes in clothes driers is also well-known in the art. For example, U.S. Pat. No. 4,073,996 discloses the use of various flexible substrate articles in clothes driers during the clothes-drying cycle in order to impart desired characteristics to the clothing being dried. Also, the '996 patent discloses the direct addition of desired additives from a spray device (e.g., an aerosol can, mechanical spray pump, or the like) using a carrier such as a propellant and/or solvent, alone or in the presence of other optional additives, such as finishing aids, fumigants, lubricants, fungicides, and sizing agents (see column 8, lines 34-35 of the '996 patent). However, no specific biocides are disclosed in this patent.

British Pat. No. 1,390,004 has shown that the addition of zinc pyrithione, in an aqueous solution of a quaternary ammonium compound during the rinse cycle of a laundering operation, results in a high degree of antimicrobial activity. However, this methodology is more expensive than might be desired since significant amounts of the zinc pyrithione are carried away with the rinsate during the rinse cycle.

U.S. Pat. No. 4,443,222 discloses the application of zinc pyrithione to cellulosic textiles by first solubilizing the zinc pyrithione in a polyamine and urea, and then impregnating the cellulosic textile with the resulting solution, and then heating the clothing to cause a specific reaction with the impregnating chemicals. This patent claims the resulting anti-microbial activity is durable to laundering. However, due to its complexity, this is not a method which lends itself to home use by a consumer on an as-needed basis.

Heretofore, there has been no disclosure in the prior art to the knowledge of the present inventors of the use of pyrithione acid, or salts thereof, as a drier-cycle additive to provide biocidal efficacy for clothing.

SUMMARY OF THE INVENTION

In one aspect, the present invention relates to a method for imparting biocidal protection to clothing or other fabrics which comprises contacting the clothing or other fabrics with a biocidally effective amount of pyrithione acid, or salt(s) thereof, or combinations thereof, in an automatic laundry dryer.

In another aspect, the present invention relates to a transfer substrate containing a biocide consisting essentially of pyrithione acid, or salt(s) thereof, or combinations thereof, said biocide being present in or on said transfer substrate in an amount sufficient to impart antimicrobial activity to clothing or other fabric in an automatic clothes dryer.

These and other aspects will become apparent upon reading the following detailed description of the invention.

DETAILED DESCRIPTION OF THE INVENTION

The pyrithione employed in the present invention is preferably selected from the group consisting of pyrithione acid, sodium pyrithione, zinc pyrithione, copper pyrithione, aluminum pyrithione, magnesium pyrithione, pyrithione disulfide, 2,2'-dithiobis-pyridine-1,1'-dioxide, chitosan pyrithione, and combinations thereof. Particularly preferred pyrithione salts useful in the present invention include sodium pyrithione, zinc pyrithione, pyrithione disulfide, and chitosan pyrithione.

The sodium pyrithione suitably employed in the process of the present invention is a well known commercial product and is commonly made by reacting 2-chloropyridine-N-oxide with NaSH and NaOH, as disclosed in U.S. Pat. No. 3,159,640, the disclosure of which is incorporated herein by reference in its entirety.

Zinc pyrithione is produced by reacting 1-hydroxy-2-pyridinethione or a soluble salt thereof with a zinc salt (eg., $ZnSO_4$) to form a zinc pyrithione precipitate, as disclosed in U.S. Pat. No. 2,809,971, incorporated herein by reference. Zinc and sodium pyrithione, as well as pyrithione disulfide and pyrithione magnesium disulfide, are commercially available under Olin Corporation's OMADINE ® registered trademark.

Chitosan pyrithione is another well-known biocide that is suitably produced in accordance with the process disclosed in U.S. Pat. No. 4,957,908, incorporated herein by reference in its entirety. Typical methods of preparing chitosan pyrithione include either reacting chitosan acetate with a pyrithione salt such as sodium pyrithione, or by neutralization of chitosan, which is a weak base, with a pyrithione acid.

The process of the present invention employs pyrithione acid, or a salt thereof, or a combination thereof to impart anti-microbial activity to fabric or textiles. The pyrithione is applied to the clothes or other fabric in the dryer, before or during the normal dryer cycle, in order to impart antimicrobial activity to the clothes or other fabric during laundering. This is accomplished by applying the pyrithione either directly using gravity or pressurized feed or aerosol spray, or indirectly using an appropriate transfer mechanism such as a transfer substrate, such as a sheet, pillow, or other substrate utilized to transfer the biocide to the clothes or other fabric during the drying cycle in the dryer. The transfer vehicle is used to transfer sufficient quantities of the pyrithione to the clothes or other fabric to impart antimicrobial activity thereto. Typically, the pyrithione is employed in the dryer in an amount sufficient to impart at least about 0.1 gram of pyrithione per laundry load in the dryer. An amount of between about 5 and about 5,000 ppm, preferably between about 5 and about 40 ppm, more preferably between about 5 and about 30 ppm, of pyrithione, based upon the weight of the clothes or other fabric being dried, is suitably imparted to the clothes or other fabric during the drying cycle in the dryer. If the transfer vehicle is a nonwoven sheet, such as a rayon sheet, the amount of pyrithione employed is between about 0.05 and about 10 grams per square foot of the said nonwoven sheet. The broad range of amounts (i e., between about 5 and about 5,000 ppm) is sufficient to impart antimicrobial activity to the clothing which inhibits the growth of unwanted microbes, including yeast, odor- and disease-causing bacteria, fungus, mildew, and the like, on the clothing or other fabric during use thereof.

Thus, fabric and textiles treated by this process exhibit growth inhibition with respect to gram (+) and gram (−) bacteria, yeast and fungi, including pathogenic organisms which are of particular concern in hospital environments.

While the invention has been described above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

EXAMPLE I

Use of Zinc Pyrithione Dispersion on a Dryer-Cycle Sheet to Impart Biocidal Efficacy to Clothes Being Dried A 48% aqueous dispersion of zinc pyrithione, commercially available as zinc OMADINE ®, a product of Olin Corporation, was diluted to 10.6% active ingredient using water. A nonwoven rayon sheet was then soaked in the said 10.6% dispersion and allowed to soak for 10 minutes. The saturated sheet was then dried for 10 minutes at 60° C. and weighed. The resultant dry weight of the zinc OMADINE and the nonwoven rayon sheet was approximately 80% of the said pyrithione. Both cotton and cotton/polyester (65/45) swatches of fabric were wet with standard tap water and wrung out to remove excess water. These were then charged to a standard household dryer with a zinc OMADINE treated nonwoven rayon sheet and dried for 30 minutes. Weight differences of foresaid swatches before and after dryer cycle were not apparent on available weighing balance, which attests to the small amount of the zinc pyrithione necessary to impart antimicrobial protection.

A Zone of Inhibition test was performed on the resulting swatches. This test measures the zone of no microbial growth surrounding a sample. An untreated sample should not produce a zone where microbial growth is inhibited. Zones were measured using *Candida albicans*—yeast, *Aspergillus niger*—mold, *Staphylococcus aureus*—gram (+) bacteria, and *Klebsiella pneumoniae*—gram (−) bacteria. Bacteria strains used in this test are recommended test organisms in the AOAC method "Bacteriostatic Activity of Laundry Additive Disinfectants".

All samples dried with the zinc pyrithione treated nonwoven rayon sheet demonstrated pronounced zones of inhibition. All samples dried with an untreated nonwoven sheet showed no signs of a zone of inhibition.

EXAMPLE II

Use of Sodium Pyrithione Dispersion on Dryer-Cycle Sheet to Impart Biocidal Efficacy to Clothes Being Dried A 40% aqueous solution of sodium pyrithione, commercially available as sodium OMADINE ®, a product of Olin Corporation was used for this procedure. A nonwoven rayon sheet was then soaked in the said 40% solution and allowed to soak for 10 minutes. The saturated sheet was then dried for 10 minutes at 60° C. and weighed. The resultant dry weight of the sodium OMADINE and the nonwoven rayon sheet was approximately 80% of the said pyrithione. Both cotton and cotton/polyester (65/45) swatches of fabric were wet with standard tap water and wrung out to remove excess water. These were then charged to a standard household dryer with a sodium OMADINE treated nonwoven rayon sheet and dried for 30 minutes. Weight differences of foresaid swatches before and after dryer cycle were not apparent on available weighing balance, which attests to the small amount of the sodium pyrithione necessary to impart antimicrobial protection.

A Zone of Inhibition test was performed on the resulting swatches. This test measures the zone of no microbial growth surrounding a sample. An untreated sample should not produce a zone where microbial growth is inhibited. Zones were measured using *Candida albicans*—yeast, *Aspergillus niger*—mold, *StaPhylococcus aureus*—gram (+) bacteria, and *Klebsiella pneumoniae*—gram (−) bacteria. Bacteria strains used in this test are recommended test organisms in the AOAC method "Bacteriostatic Activity of Laundry Additive Disinfectants".

All samples dried with the sodium pyrithione treated nonwoven rayon sheet demonstrated pronounced zones of inhibition. All samples dried with an untreated nonwoven sheet showed no signs of a zone of inhibition.

Having thus described the invention, what is claimed is:

1. A method for imparting biocidal protection to clothing or other fabric which comprises contacting the clothing or other fabrics with a composition consisting essentially of a biocidally effective amount of a biocide consisting essentially of pyrithione acid, or salt(s) thereof, or combinations thereof, in an automatic laundry dryer, wherein said biocidally effective amount is between about 5 and about 5,000 ppm based upon the weight of said contacting is effected by means of a transfer sheet, wherein said transfer sheet contains pyrithione in an amount of between about 0.05 and about 10 grams per square foot of said transfer sheet, and wherein said salt (s) is selected from the group consisting of sodium pyrithione, zinc pyrithione, copper pyrithione, aluminum pyrithione, magnesium pyrithione, pyrithione disulfide, 2,2'-dithiobis-pyridine-1,1'-dioxide, chitosan pyrithione, and combinations thereof.

2. The process of claim 1 wherein said biocidally effective amount is between about 5 and about 40 ppm based upon the weight of said clothing or other fabric in said laundry dryer.

* * * * *

UNITED STATES PATENT AND TRADEMARK OFFICE
CERTIFICATE OF CORRECTION

PATENT NO. : 5,154,947
DATED : October 13, 1992
INVENTOR(S) : Branch et al.

It is certified that error appears in the above-identified patent and that said Letters Patent is hereby corrected as shown below:

In column 4, at line 51 after "said" and before "contacting" please insert --clothing or other fabric in said laundry dryer, wherein said--.

Signed and Sealed this

Fifth Day of October, 1993

Attest:

BRUCE LEHMAN

Attesting Officer  Commissioner of Patents and Trademarks